(12) United States Patent
Pianca

(10) Patent No.: US 8,887,387 B2
(45) Date of Patent: Nov. 18, 2014

(54) METHODS OF MANUFACTURE OF LEADS WITH A RADIALLY SEGMENTED ELECTRODE ARRAY

(75) Inventor: Anne Margaret Pianca, Santa Monica, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 1021 days.

(21) Appl. No.: 12/498,650

(22) Filed: Jul. 7, 2009

(65) Prior Publication Data

US 2011/0005069 A1    Jan. 13, 2011

(51) Int. Cl.
*H01R 43/00* (2006.01)
*A61N 1/05* (2006.01)

(52) U.S. Cl.
CPC ............. *H01R 43/00* (2013.01); *A61N 1/0534* (2013.01); *A61N 1/05* (2013.01)
USPC .................. 29/858; 29/847; 29/883; 29/884; 607/117

(58) Field of Classification Search
CPC ..... A61N 1/05; A61N 1/0534; A61N 1/0541; H01R 43/00
USPC .................. 600/373, 393, 395; 607/116, 118; 29/825, 843, 844, 848, 857, 858, 860, 29/861, 874, 882–884, 834
See application file for complete search history.

(56) References Cited

U.S. PATENT DOCUMENTS

| | | | |
|---|---|---|---|
| 3,972,548 A | 8/1976 | Roseen et al. | |
| 4,602,624 A | 7/1986 | Naples et al. | |
| 4,630,611 A | 12/1986 | King | |
| 4,744,370 A | 5/1988 | Harris | |
| 4,762,135 A * | 8/1988 | van der Puije et al. | 607/116 |
| 5,000,194 A | 3/1991 | van den Honert et al. | |
| 5,016,646 A | 5/1991 | Gotthardt et al. | |
| 5,135,001 A | 8/1992 | Sinofsky et al. | |

(Continued)

FOREIGN PATENT DOCUMENTS

| | | |
|---|---|---|
| EP | 0580928 A1 | 2/1994 |
| EP | 0650694 B1 | 7/1998 |

(Continued)

OTHER PUBLICATIONS

International Search Report and Written Opinion for International Patent Application No. PCT/US2011/058160 mailed Mar. 19, 2012.

(Continued)

*Primary Examiner* — Donghai D Nguyen
(74) *Attorney, Agent, or Firm* — Lowe Graham Jones PLLC; Bruce E. Black

(57) ABSTRACT

A method of making a lead for a stimulation device includes forming at least one pre-electrode in the shape of a ring, the at least one pre-electrode comprises at least two thin-walled portions separated by at least two thick-walled portions; disposing the at least one pre-electrode near a distal end of a lead body; joining at least one conductor to each thick-walled portion of the at least one pre-electrode; and grinding the lead body and the at least one pre-electrode to remove the thin-walled portions of the at least one pre-electrode to form segmented electrodes from the thick-walled portions of the at least one pre-electrode.

19 Claims, 12 Drawing Sheets

(56) References Cited

U.S. PATENT DOCUMENTS

| | | | |
|---|---|---|---|
| 5,199,433 A * | 4/1993 | Metzger et al. | 600/393 |
| 5,374,285 A | 12/1994 | Vaiani et al. | |
| 5,458,629 A | 10/1995 | Baudino et al. | |
| 5,522,874 A | 6/1996 | Gates | |
| 5,711,316 A | 1/1998 | Elsberry et al. | |
| 5,713,922 A | 2/1998 | King | |
| 5,800,350 A | 9/1998 | Coppleson et al. | |
| 5,843,148 A | 12/1998 | Gijsbers et al. | |
| 5,938,688 A | 8/1999 | Schiff | |
| 5,987,361 A | 11/1999 | Mortimer | |
| 6,018,684 A | 1/2000 | Bartig et al. | |
| 6,134,478 A | 10/2000 | Spehr | |
| 6,161,047 A | 12/2000 | King et al. | |
| 6,167,311 A | 12/2000 | Rezai | |
| 6,181,969 B1 | 1/2001 | Gord | |
| 6,322,559 B1 | 11/2001 | Daulton et al. | |
| 6,510,347 B2 | 1/2003 | Borkan | |
| 6,516,227 B1 | 2/2003 | Meadows et al. | |
| 6,556,873 B1 | 4/2003 | Smits | |
| 6,564,078 B1 | 5/2003 | Marino et al. | |
| 6,609,029 B1 | 8/2003 | Mann et al. | |
| 6,609,032 B1 | 8/2003 | Woods et al. | |
| 6,678,564 B2 | 1/2004 | Ketterl et al. | |
| 6,723,113 B1 | 4/2004 | Shkolnik | |
| 6,741,892 B1 | 5/2004 | Meadows et al. | |
| 6,757,970 B1 | 7/2004 | Kuzma et al. | |
| 7,027,852 B2 | 4/2006 | Helland | |
| 7,047,081 B2 | 5/2006 | Kuzma | |
| 7,047,082 B1 | 5/2006 | Schrom et al. | |
| 7,047,084 B2 | 5/2006 | Erickson et al. | |
| 7,051,419 B2 | 5/2006 | Schrom et al. | |
| 7,212,867 B2 | 5/2007 | Van Venrooij et al. | |
| 7,292,890 B2 | 11/2007 | Whitehurst et al. | |
| 7,489,971 B1 | 2/2009 | Franz | |
| 7,668,601 B2 | 2/2010 | Hegland et al. | |
| 7,761,985 B2 | 7/2010 | Hegland et al. | |
| 7,809,446 B2 | 10/2010 | Meadows | |
| 7,840,188 B2 | 11/2010 | Kurokawa | |
| 7,848,802 B2 | 12/2010 | Goetz | |
| 7,856,707 B2 | 12/2010 | Cole | |
| 7,860,570 B2 | 12/2010 | Whitehurst et al. | |
| 7,974,705 B2 | 7/2011 | Zdeblick et al. | |
| 7,979,140 B2 | 7/2011 | Schulman | |
| 8,000,808 B2 | 8/2011 | Hegland et al. | |
| 8,019,440 B2 | 9/2011 | Kokones et al. | |
| 8,036,755 B2 | 10/2011 | Franz | |
| 8,041,309 B2 | 10/2011 | Kurokawa | |
| 8,099,177 B2 | 1/2012 | Dahlberg | |
| 8,225,504 B2 | 7/2012 | Dye et al. | |
| 8,295,944 B2 | 10/2012 | Howard et al. | |
| 8,321,025 B2 | 11/2012 | Bedenbaugh | |
| 8,583,237 B2 | 11/2013 | Bedenbaugh | |
| 2002/0156513 A1 | 10/2002 | Borkan | |
| 2002/0183817 A1 | 12/2002 | Van Venrooij et al. | |
| 2004/0039434 A1 | 2/2004 | Schrom et al. | |
| 2004/0059392 A1 | 3/2004 | Parramon et al. | |
| 2005/0015130 A1 | 1/2005 | Gill | |
| 2005/0038489 A1 | 2/2005 | Grill | |
| 2005/0171587 A1 | 8/2005 | Daglow et al. | |
| 2006/0025841 A1 | 2/2006 | McIntyre | |
| 2006/0149335 A1 | 7/2006 | Meadows | |
| 2006/0168805 A1 | 8/2006 | Hegland et al. | |
| 2006/0173262 A1 | 8/2006 | Hegland et al. | |
| 2006/0247697 A1 | 11/2006 | Sharma et al. | |
| 2007/0150007 A1 | 6/2007 | Anderson et al. | |
| 2007/0150036 A1 | 6/2007 | Anderson | |
| 2007/0161294 A1 | 7/2007 | Brase et al. | |
| 2007/0168008 A1 | 7/2007 | Olsen | |
| 2007/0203537 A1 | 8/2007 | Goetz et al. | |
| 2007/0203538 A1 | 8/2007 | Stone et al. | |
| 2007/0203539 A1 | 8/2007 | Stone et al. | |
| 2007/0203540 A1 | 8/2007 | Goetz et al. | |
| 2007/0203541 A1 | 8/2007 | Goetz et al. | |
| 2007/0203542 A1 | 8/2007 | Goetz et al. | |
| 2007/0203543 A1 | 8/2007 | Stone et al. | |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0219595 A1 | 9/2007 | He |
| 2007/0239243 A1 | 10/2007 | Moffitt et al. |
| 2007/0265664 A1 | 11/2007 | Gerber et al. |
| 2008/0071320 A1 | 3/2008 | Brase |
| 2008/0103574 A1 | 5/2008 | Gerber |
| 2008/0103580 A1 | 5/2008 | Gerber |
| 2008/0114230 A1 | 5/2008 | Addis |
| 2008/0140168 A1 | 6/2008 | Walter et al. |
| 2008/0215125 A1 | 9/2008 | Farah et al. |
| 2008/0269740 A1 | 10/2008 | Bonde et al. |
| 2008/0269854 A1 | 10/2008 | Hegland et al. |
| 2009/0012591 A1 | 1/2009 | Barker |
| 2009/0054936 A1 | 2/2009 | Eggen et al. |
| 2009/0054941 A1 | 2/2009 | Eggen et al. |
| 2009/0054946 A1 | 2/2009 | Sommer et al. |
| 2009/0054947 A1 | 2/2009 | Bourn et al. |
| 2009/0082640 A1 | 3/2009 | Kovach et al. |
| 2009/0082641 A1 | 3/2009 | Giftakis et al. |
| 2009/0082829 A1 | 3/2009 | Panken et al. |
| 2009/0083070 A1 | 3/2009 | Giftakis et al. |
| 2009/0105785 A1 | 4/2009 | Wei et al. |
| 2009/0112282 A1 | 4/2009 | Kast et al. |
| 2009/0187222 A1 | 7/2009 | Barker |
| 2009/0204192 A1 | 8/2009 | Carlton et al. |
| 2009/0204193 A1 | 8/2009 | Kokones et al. |
| 2009/0276021 A1 | 11/2009 | Meadows et al. |
| 2010/0036468 A1 | 2/2010 | Decre et al. |
| 2010/0076535 A1 | 3/2010 | Pianca et al. |
| 2010/0082076 A1 | 4/2010 | Lee et al. |
| 2010/0094387 A1 | 4/2010 | Pianca et al. |
| 2010/0268298 A1 | 10/2010 | Moffitt et al. |
| 2010/0269339 A1 | 10/2010 | Dye et al. |
| 2011/0047795 A1 | 3/2011 | Turner et al. |
| 2011/0056076 A1 | 3/2011 | Hegland et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 02068042 A1 | 9/2002 |
| WO | 2004045707 A1 | 6/2004 |
| WO | 2008053789 A1 | 5/2008 |
| WO | 2009-001327 A2 | 12/2008 |
| WO | 2009025816 A1 | 2/2009 |
| WO | 2009102536 A1 | 8/2009 |
| WO | 2010055421 A1 | 5/2010 |

OTHER PUBLICATIONS

U.S. Appl. No. 12/237,888, filed Sep. 25, 2008.
U.S. Appl. No. 12/177,823, filed Jul. 22, 2008.
U.S. Appl. No. 61/170,037, filed Apr. 16, 2009.
U.S. Appl. No. 11/238,240, filed Sep. 28, 2005.
U.S. Appl. No. 11/694,769, filed Mar. 30, 2007.
U.S. Appl. No. 11/855,033, filed Sep. 13, 2007.

(56) References Cited

OTHER PUBLICATIONS

Cameron, T. "Safety and Efficacy of Spinal Cord Stimulation for the Treatment of Chronic Pain: a 20-year Review". J. Neurosurg Spine 2004,:100: 254-267.
Rosenow, J.M, et al. "Failure modes of spinal cord stimulation hardware." J Neurosurg Spine 2006; 5: 183-190.
U.S. Appl. No. 13/275,112, filed Oct. 17, 2011.
U.S. Appl. No. 13/363,059, filed Jan. 31, 2012.
U.S. Appl. No. 13/368,982, filed Feb. 8, 2012.
U.S. Appl. No. 13/369,013, filed Feb. 8, 2012.
U.S. Appl. No. 13/368,733, filed Feb. 8, 2012.
International Search Report and Written Opinion for International Patent Application No. PCT/US2010/040995 mailed Jan. 18, 2011.
International Preliminary Report on Patentability for International Patent Application No. PCT/US2010/040995 mailed Jan. 19, 2012.
U.S. Appl. No. 13/951,057, filed Jul. 25, 2013.
U.S. Appl. No. 14/053,112, filed Oct. 14, 2013.
U.S. Appl. No. 13/750,725, filed Jan. 25, 2013.
U.S. Appl. No. 13/787,171, filed Mar. 6, 2013.
U.S. Appl. No. 13/899,316, filed May 21, 2013.
U.S. Appl. No. 13/906,776, filed May 31, 2013.
Official Communication for U.S. Appl. No. 12/966,740 mailed Apr. 24, 2014.

* cited by examiner

METHODS OF MANUFACTURE OF LEADS WITH A RADIALLY SEGMENTED ELECTRODE ARRAY

FIELD

The invention is directed to methods for brain stimulation including deep brain stimulation. In addition, the invention is directed to methods for manufacturing a lead for brain stimulation having a plurality of segmented electrodes.

BACKGROUND

Deep brain stimulation can be useful for treating a variety of conditions including, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging (MRI) or computerized tomography (CT) scans can provide a starting point for determining where the stimulating electrode should be positioned to provide the desired stimulus to the target neurons.

Upon insertion, current is introduced along the length of the lead to stimulate target neurons in the brain. This stimulation is provided by electrodes, typically in the form of rings, disposed on the lead. The current projects from each electrode equally in every direction at any given length along the axis of the lead. Because of the shape of the electrodes, radial selectivity of the current is minimal. This results in the unwanted stimulation of neighboring neural tissue, undesired side effects and an increased duration of time for the proper therapeutic effect to be obtained.

Studies have shown that current methods of manufacture produce deep brain stimulation leads that are unreliable and prone to failure. One study shows that lead breakage rates for some lead products are reported anywhere from 6.8-12.4%, and that the breakage occurs on average from 260-390 days. Thus in many cases, revision surgery is needed within a short period of time. This revision surgery is physically, mentally and financially taxing on the patient.

BRIEF SUMMARY

In some embodiments, a method of making a lead for a stimulation device includes forming at least one pre-electrode in the shape of a ring, the at least one pre-electrode comprises at least two thin-walled portions separated by at least two thick-walled portions; disposing the at least one pre-electrode near a distal end of a lead body, joining at least one conductor to each thick-walled portion of the at least one pre-electrode; and grinding the lead body and the at least one pre-electrode to remove the thin-walled portions of the at least one pre-electrode to form a plurality of segmented electrodes from the thick-walled portions of the at least one pre-electrode.

In some embodiments, a method of making a lead for a stimulation device includes coupling a plurality of electrodes to a temporary plate; joining individual conductors to each of the plurality of electrodes; forming the temporary plate into a cylinder with the conductors extending through a lumen of the cylinder; filling the lumen of the cylinder with an insulative material to create a lead assembly; and removing the temporary plate having the plurality of electrodes exposed.

In some embodiments, a method of making a lead for a stimulation device includes disposing a plurality of electrodes in a mold and overmolding in a flexible carrier; removing the flexible carrier and electrodes from the mold; joining conductors to the plurality of electrodes to form a carrier; shaping the carrier into a substantially cylindrical shape; and joining the carrier to a lead body.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of devices and methods for brain stimulation including deep brain stimulation. In addition, the invention is directed to methods for manufacturing a lead for brain stimulation having a plurality of segmented electrodes.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in the art. See, for instance, U.S. Patent Application Publication No. 2006/0149335 A1 ("Devices and Methods For Brain Stimulation"), U.S. patent application Ser. No. 12/237,888 ("Leads With Non-Circular-Shaped Distal Ends For Brain Stimulation Systems and Methods of Making and Using"), U.S. Patent Application Publication 2007/0150036 A1 ("Stimulator Leads and Methods For Lead Fabrication"), U.S. patent application Ser. No. 12/177,823 ("Lead With Transition and Methods of Manufacture and Use"), U.S. patent application Ser. No. 12/427,935 ("Electrodes For Stimulation Leads and Methods of Manufacture and Use"), and U.S. Patent Application Ser. No. 61/170,037 entitled "Deep Brain Stimulation Current Steering with Split Electrodes." Each of these references is incorporated herein by reference in its respective entirety.

Figure 12:
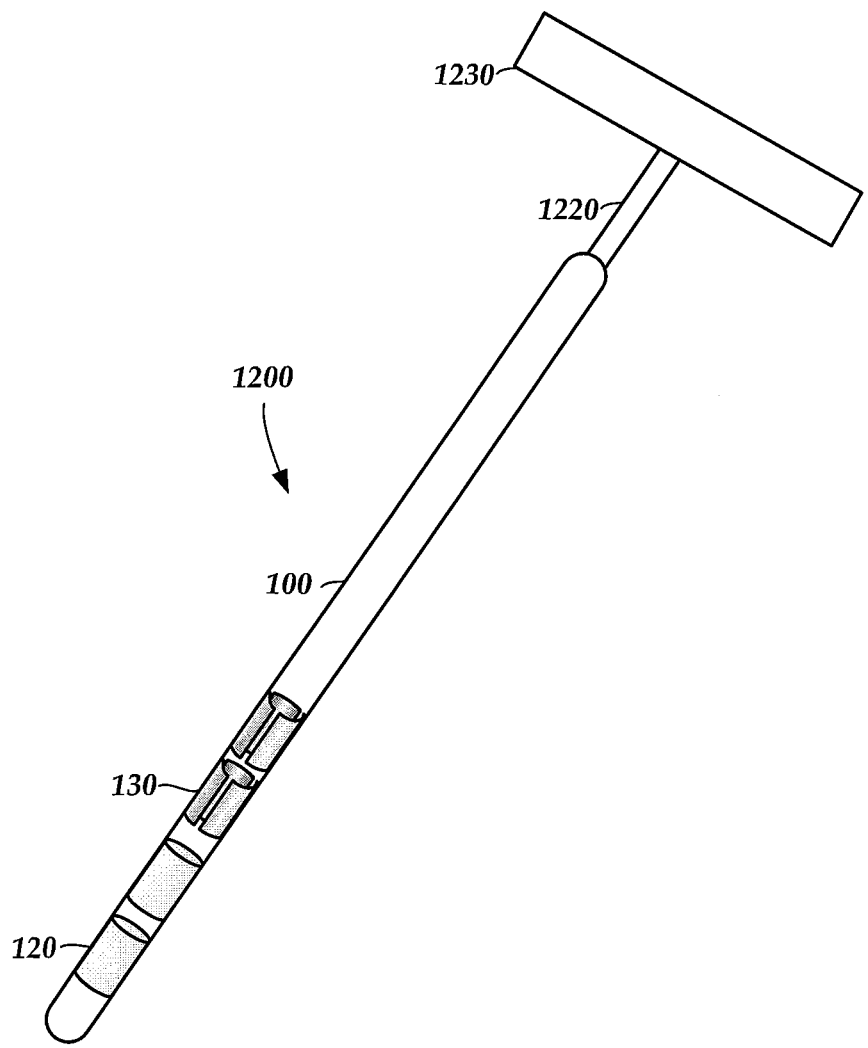
FIG. 12 is a schematic side view of one embodiment of a lead and a stylet, according to the invention.

FIG. 12 illustrates one embodiment of a device 1200 for brain stimulation. The device includes a lead 100, ring electrodes 120, segmented electrodes 130, and a stylet 1220 for assisting in insertion and positioning of the lead in the patient's brain. The stylet 1220 can be made of a rigid material. Examples of suitable materials include tungsten, stainless steel, or plastic. The stylet 1220 may have a handle 1230 to assist insertion into the lead, as well as rotation of the stylet and lead. A proximal end is coupled to, or coupleable to, a control unit.

In one example of operation, access to the desired position in the brain can be accomplished by drilling a hole in the patient's skull or cranium with a cranial drill (commonly referred to as a burr), and coagulating and incising the dura mater, or brain covering. The lead 100 can be inserted into the cranium and brain tissue with the assistance of the stylet 1220. The lead can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): rotate the lead, insert the lead, or retract the lead. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 100 for deep brain stimulation can include stimulation electrodes, recording electrodes, or both. In at least some embodiments, the lead is rotatable so that the stimulation electrodes can be aligned with the target neurons after the neurons have been located using the recording electrodes.

Stimulation electrodes may be disposed on the circumference of the lead to stimulate the target neurons. Stimulation electrodes may be ring-shaped so that current projects from each electrode equally in every direction at any given length along the axis of the lead. To achieve current steering, segmented electrodes can be utilized additionally or alternatively. Though the following description discusses stimulation electrodes, it will be understood that all configurations of the stimulation electrodes discussed may be utilized in arranging recording electrodes as well.

Figure 1:
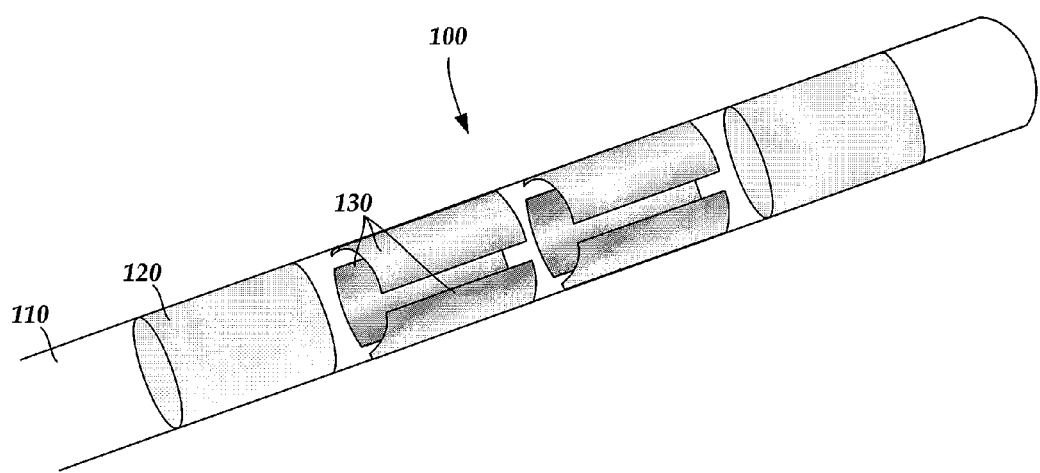
FIG. 1 is a schematic perspective view of one embodiment of a portion of a lead having a plurality of segmented electrodes, according to the invention.

FIG. 1 illustrates one embodiment of a lead 100 for brain stimulation. The device includes a lead body 110, one or more optional ring electrodes 120, and a plurality of segmented electrodes 130. The lead body 110 can be formed of a biocompatible, non-conducting material such as, for example, a polymeric material. Suitable polymeric materials include, but are not limited to, silicone, polyurethanes, polyethylene, polyureas, or polyurethane-ureas. In at least some instances, the lead may be in contact with body tissue for extended periods of time. In at least some embodiments, the lead has a cross-sectional diameter of no more than 1.5 mm and may be in the range of 1 to 1.5 mm in at least some embodiments, the lead has a length of at least 10 cm and the length of the lead may be in the range of 25 to 70 cm.

In at least some embodiments, stimulation electrodes may be disposed on the lead body 110. These stimulation electrodes may be made using a metal, alloy, conductive oxide, or any other suitable conductive biocompatible material. Examples of suitable materials include, but are not limited to, platinum, platinum iridium alloy, iridium, titanium, or tungsten. Preferably, the stimulation electrodes are made of a material that is biocompatible and does not substantially corrode under expected operating conditions in the operating environment for the expected duration of use.

In at least some embodiments, any of the electrodes can be used as an anode or cathode and carry anodic or cathodic current. In some instances, an electrode might be an anode for a period of time and a cathode for a period of time. In other embodiments, the identity of a particular electrode or electrodes as an anode or cathode might be fixed.

Stimulation electrodes in the form of ring electrodes 120 may be disposed on any part of the lead body 110, usually near a distal end of the lead. FIG. 1 illustrates a portion of a lead having two ring electrodes. Any number of ring electrodes, or even a single ring electrode, may be disposed along the length of the lead body 110. For example, the lead body may have one ring electrode, two ring electrodes, three ring electrodes or four ring electrodes. In some embodiments, the lead will have five, six, seven or eight ring electrodes. It will be understood that any number of ring electrodes may be disposed along the length of the lead body 110. In some embodiments, the ring electrodes 120 are substantially cylindrical and wrap around the entire circumference of the lead body 110. In some embodiments, the outer diameter of the ring electrodes 120 is substantially equal to the outer diameter of the lead body 110. The width of ring electrodes 120 may vary according to the desired treatment and the location of the target neurons. In some embodiments the width of the ring electrode 120 is less than or equal to the diameter of the ring electrode 120. In other embodiments, the width of the ring electrode 120 is greater than the diameter of the ring electrode 120.

Deep brain stimulation leads having segmented electrodes provide for superior current steering because target structures in deep brain stimulation are not symmetric about the axis of the distal electrode array. Instead, a target may be located on one side of a plane running through the axis of the lead. Through the use of a radially segmented electrode array (RSEA), current steering can be performed along the axis of the lead but also around the circumference of the lead.

The lead contains a plurality of segmented electrodes 130. Any number of segmented electrodes 130 may be disposed on the lead body 110. In some embodiments, the segmented electrodes 130 are grouped in sets of segmented electrodes, each set disposed around the circumference of the lead at a particular longitudinal position. The lead may have any number of sets of segmented electrodes. In at least some embodiments, the lead has one, two, three, four, five, six, seven, or eight sets of segmented electrodes. In at least some embodiments, each set of segmented electrodes contains the same number of segmented electrodes 130. In some embodiments, each set of segmented electrodes contains three segmented electrodes 130. In at least some other embodiments, each set of segmented electrodes contains two, four, five, six, seven or eight segmented electrodes. The segmented electrodes 130 may vary in size and shape. In some embodiments, the segmented electrodes 130 are all of the same size, shape, diameter, width or area or any combination thereof. In some embodiments, the segmented electrodes of each set (or even all segmented electrodes) may be identical in size and shape.

Each set of segmented electrodes 130 may be disposed around the circumference of the lead body 110 to form a substantially cylindrical shape around the lead body 110. The spacing of the segmented electrodes 130 around the circumference of the lead body 110 may vary as will be described with reference to FIGS. 7B, 8B and 9B. In at least some embodiments, equal spaces, gaps or cutouts are disposed between each segmented electrodes 130 around the circumference of the lead body 110. In other embodiments, the spaces, gaps or cutouts between segmented electrodes may differ in size or shape. In other embodiments, the spaces, gaps, or cutouts between segmented electrodes may be uniform for a particular set of segmented electrodes or for all sets of segmented electrodes. The segmented electrodes 130 may be positioned in irregular or regular intervals around the lead body 110.

Conductors (not shown) that attach to or from the ring electrodes 120 and segmented electrodes 130 also pass through the lead body 110. These conductors may pass through the material of the lead or through a lumen defined by the lead. The conductors are presented at a connector for coupling of the electrodes to a control unit (not shown). In one embodiment, the stimulation electrodes correspond to wire conductors that extend out of the lead body 110 and are then trimmed or ground down flush with the lead surface. The conductors may be coupled to a control unit to provide stimulation signals, often in the form of pulses, to the stimulation electrodes.

Figure 2:
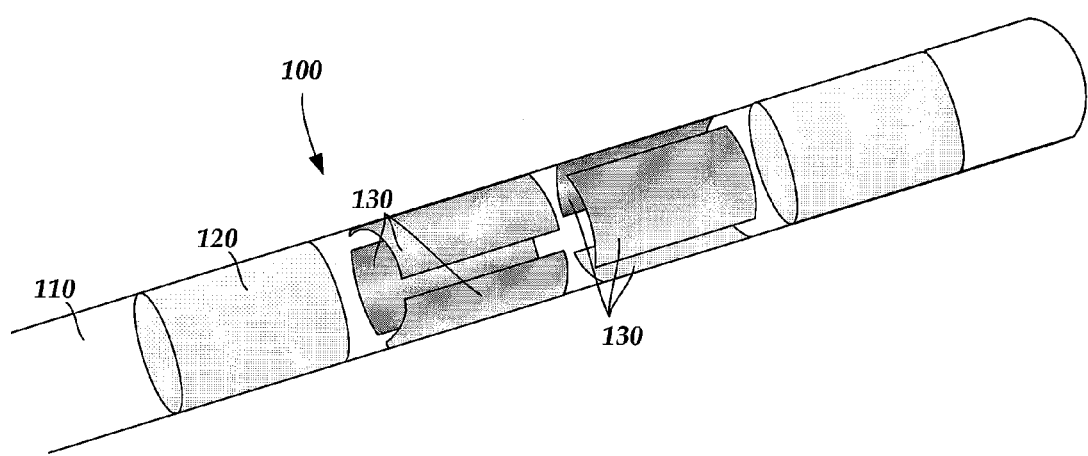
FIG. 2 is a schematic perspective view of another embodiment of a portion of a lead having a plurality of segmented electrodes arranged in a staggered orientation, according to the invention.

FIG. 2 is a schematic side view of another embodiment of a lead having a plurality of segmented electrodes. As seen in FIG. 2, the plurality of segmented electrodes 130 may be arranged in different orientations relative to each other. In contrast to FIG. 1, where the two sets of segmented electrodes are aligned along the length of the lead body 110, FIG. 2 displays another embodiment in which the two sets of segmented electrodes 130 are staggered. In at least some embodiments, the sets of segmented electrodes are staggered such that no segmented electrodes are aligned along the length of the lead body 110. In some embodiments, the segmented electrodes may be staggered so that at least one of the segmented electrodes is aligned with another segmented electrode of a different set, and the other segmented electrodes are not aligned.

Figure 3A:
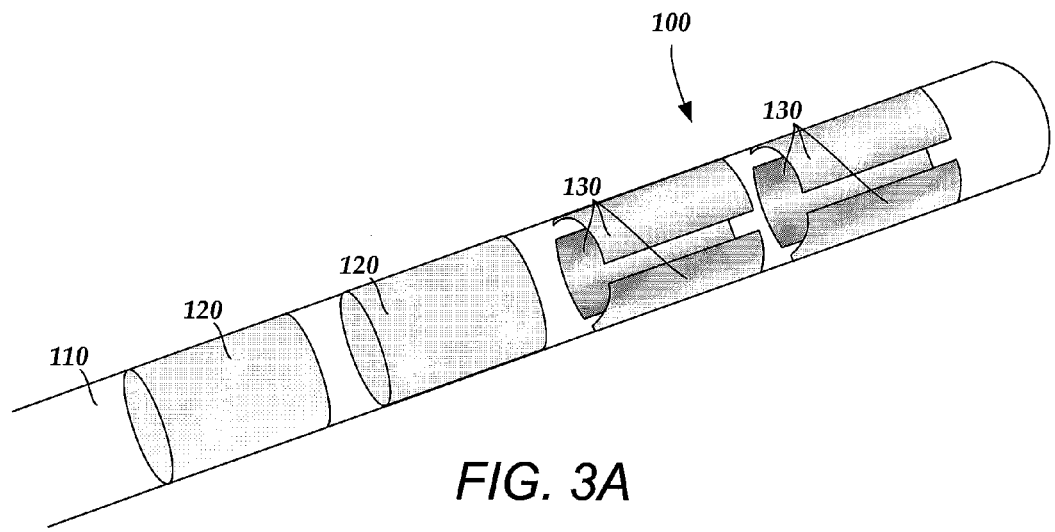
FIG. 3A is a schematic perspective view of a third embodiment of a portion of a lead having a plurality of segmented electrodes, according to the invention.
Figure 3B:
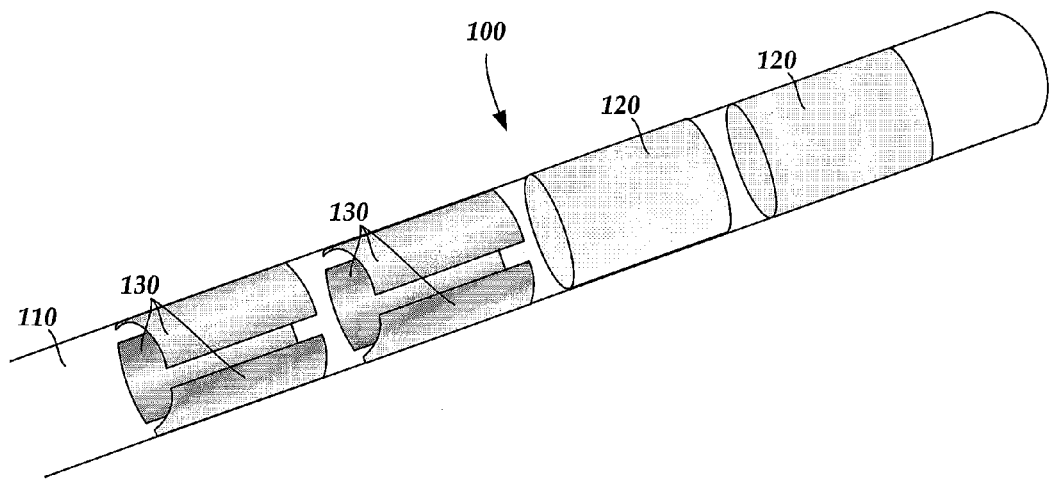
FIG. 3B is a schematic perspective view of a fourth embodiment of a portion of a lead having a plurality of segmented electrodes, according to the invention.

Any number of segmented electrodes 130 may be disposed on the lead body 110 in any number of sets. FIGS. 1 and 2 illustrate embodiments including two sets of segmented electrodes. These two sets of segmented electrodes 130 may be disposed in different configurations. FIG. 3A is a schematic perspective view of a third embodiment of a lead having a plurality of segmented electrodes. The lead body 110 of FIG. 3A has a proximal end and a distal end. As will be appreciated from FIG. 3A, the two sets of segmented electrodes 130 are disposed on the distal end of the lead body 110, distal to the two ring electrodes 120. FIG. 3B is a schematic perspective view of a fourth embodiment of a lead body 110. In FIG. 3B, the two sets of segmented electrodes 130 are disposed proximal to the two ring electrodes 120. By varying the location of the segmented electrodes 130, different coverage of the target neurons may be selected. For example, the electrode arrangement of FIG. 3A may be useful if the physician anticipates that the neural target will be closer to the distal tip of the lead body 110, while the electrode arrangement of FIG. 3B may be useful if the physician anticipates that the neural target will be closer to the proximal end of the lead body 110. In at least some embodiments, the ring electrodes 120 alternate with sets of segmented electrodes 130.

Any combination of ring electrodes 120 and segmented electrodes 130 may be disposed on the lead. In some embodiments the segmented electrodes are arranged in sets. For example, a lead may include a first ring electrode 120, two sets of segmented electrodes, each set formed of three segmented electrodes 130, and a final ring electrode 120 at the end of the lead. This configuration may simply be referred to as a 1-3-3-1 configuration. It may be useful to refer to the electrodes with this shorthand notation. Thus, the embodiment of FIG. 3A may be referred to as a 1-1-3-3 configuration, while the embodiment of FIG. 3B may be referred to as a 3-3-1-1 configuration. Other eight electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. In some embodiments, the lead will have 16 electrodes. Possible configurations for a 16-electrode lead include, but are not limited to 4-4-4-4, 8-8, 3-3-3-3-3-1 (and all rearrangements of this configuration), and 2-2-2-2-2-2-2-2.

Figure 4:
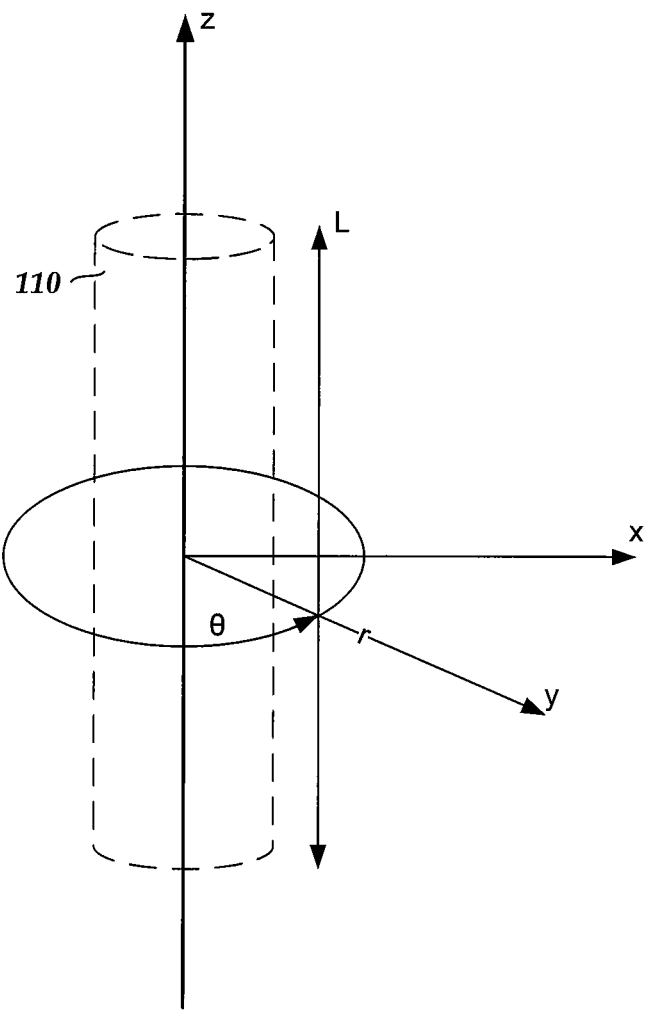
FIG. 4 is a schematic diagram of radial current steering along various electrode levels along the length of a lead, according to the invention.

FIG. 4 is a schematic diagram to illustrate radial current steering along various electrode levels along the length of a lead. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead body 110. In some embodiments, the radial distance, r, and the angle θ around the circumference of the lead body 110 may be dictated by the percentage of anodic current (recognizing that stimulation predominantly occurs near the cathode, although strong anodes may cause stimulation as well) introduced to each electrode as will be described in greater detail below. In at least some embodiments, the configuration of anodes and cathodes along the segmented electrodes 130 allows the centroid of stimulation to be shifted to a variety of different locations along the lead body 110.

As can be appreciated from FIG. 4, the centroid of stimulation can be shifted at each level along the length of the lead. The use of multiple sets of segmented electrodes 130 at different levels along the length of the lead allows for three-dimensional current steering. In some embodiments, the sets of segmented electrodes 130 are shifted collectively (i.e. the centroid of simulation is similar at each level along the length of the lead). In at least some other embodiments, each set of segmented electrodes 130 is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 130 are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods for manufacturing leads that have demonstrated very low incidents of lead breakage.

Figure 5:
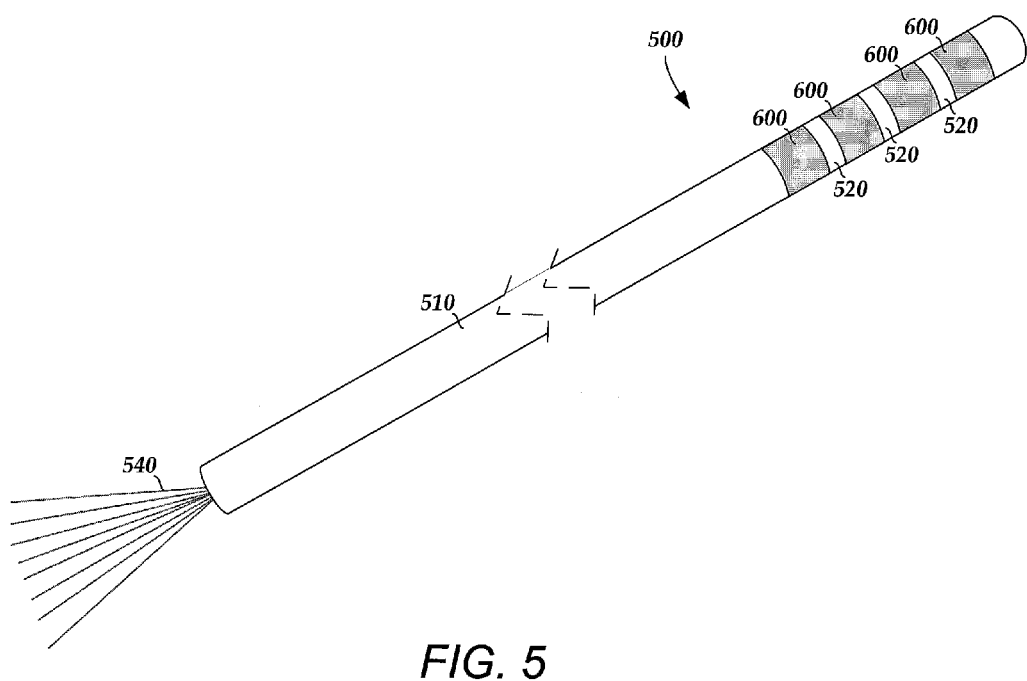
FIG. 5 is a perspective view of a portion of a lead having conductors cables exposed at the distal end, according to the invention.

In some embodiments, fabrication of a lead begins with the proximal end. FIG. 5 is a perspective view of a portion of a lead 500 having conductors 540 exposed at the distal end of the lead body 510. As described above with reference to FIG. 1, the conductors 540 attach to or from pre-electrodes 600 and also pass through the lead body 510. These conductors may pass through the material of the lead or through a lumen defined by the lead. In some embodiments, the stimulation or recording electrodes correspond to wire conductors that extend out of the lead body 510 and are then trimmed or ground down flush with the lead surface. The conductors 540 may further be coupled to terminals (not shown). The terminals are typically disposed at the proximal end of the one or more lead bodies for connection to corresponding connector contacts in connectors disposed on, for example, a control module (or to other devices, such as connector contacts on a lead extension, an operating room cable, or an adaptor). Furthermore, the control module may provide stimulation signals, often in the form of pulses, to the stimulation electrodes. The length of the lead body 510 and the conductors 540 exposed at the distal end may vary as required for the final product configuration.

Figure 6:
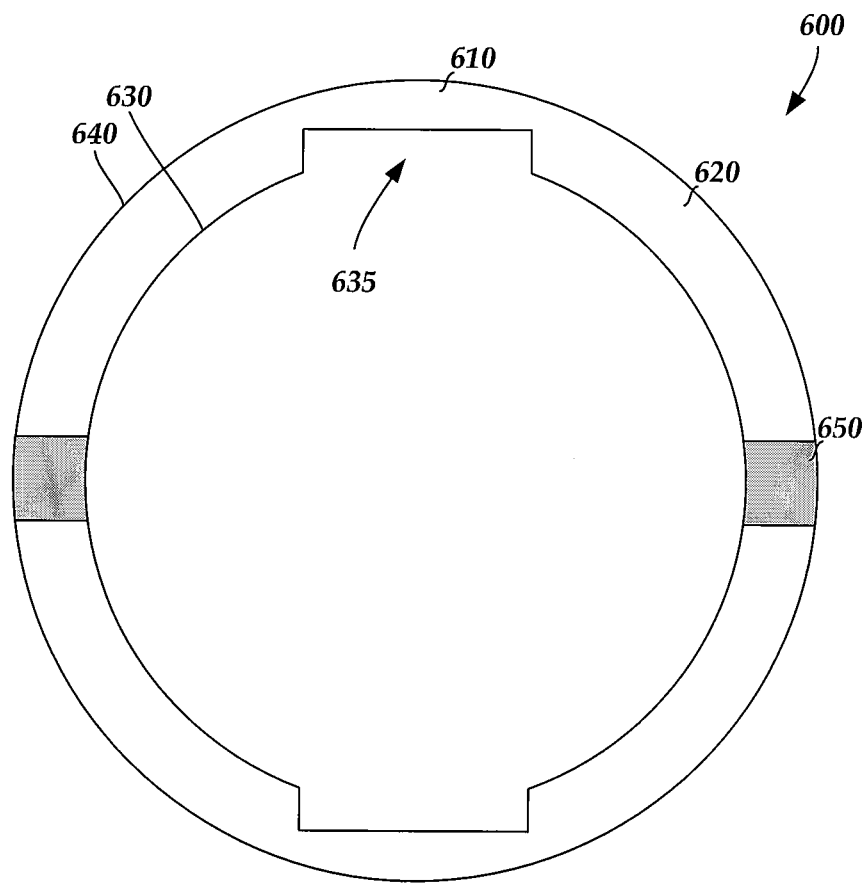
FIG. 6 is a schematic cross-sectional view of a pre-electrode having two thin-walled portions separated by two thick-walled portions, according to the invention.

In some embodiments, fabrication of a radially segmented electrode array begins with a pre-electrode, from which segmented electrodes are formed. FIG. 6 is a schematic cross-sectional view of a pre-electrode 600. In some embodiments, as seen in FIG. 6, the pre-electrode 600 has two thin-walled portions 610 separated by two thick-walled portions 620. The thin-walled portions 610 and thick-walled portions 620 may be formed by creating an inner diameter 630 and an outer diameter 640. In some embodiments, the outer diameter 640 is isodiametric, but the inner diameter 630 is not isodiametric. Instead, the inner diameter 630 may have an irregular diameter including, for example, keyed portions 635 where the inner diameter is larger than the remaining portions or where portions of the pre-electrode 600 have been removed or are unformed. The keyed portions 635 may be the result of a sudden change in diameter as seen in FIG. 6 or a more gradual change in diameter.

The resulting thin-walled portions 610 and thick-walled portions 620 may vary in size. In some embodiments, the thin-walled portions 610 and thick-walled portions 620 are of equal radial size. In at least some other embodiments, the majority of the circumference of the pre-electrode 600 forms the thick-walled portions 620. As seen in FIG. 6, in some embodiments, two thick-walled portions and two thin-walled portions are formed. In some embodiments, the thin-walled portions 610 are of equal radial size. In some embodiments, the thick-walled portions 620 are of equal radial size. It will be understood that in at least some other embodiments, one thick-walled portion may be formed larger than another thick-walled portion.

In some embodiments, the lead body 510 of FIG. 5 includes ablated sections for receiving the pre-electrodes 600 of FIG. 6. In some embodiments, the ablated sections of the lead body are disposed on the distal end of the lead body 510, particularly portions of the lead body 510 disposed under the pre-electrodes 600. In some embodiments, slots, grit, sand-blasted or roughened regions, or a coating such as titanium nitride may be added to the pre-electrodes 600, in particular the inner diameter, to increase adhesion to the leady body 510. Conductors may then be coupled to the pre-electrodes 600. In some embodiments, the conductors are welded to the pre-electrodes 600 though it will be understood that any suitable method of coupling the pre-electrodes to the conductors may be utilized, such as laser welding, resistance welding, conductive epoxy, and the like. As seen in FIG. 6, the pre-electrode 600 may include slotted positions 650 for positioning of the conductor and welding. In some embodiments, a plurality of slotted positions may be disposed on the pre-electrode 600, so that each portion of the pre-electrode 600 is connected to a conductor. In at least some embodiments, as seen in FIG. 6, the slotted positions 650 are disposed on opposite sides of the pre-electrode 600.

In some embodiments, spacers 520 are disposed next to each pre-electrode 600 along the length of the lead body 510. The spacers 520 may be disposed between the pre-electrodes 600 and may have a hollow center area such that the spacers 520 can be threaded onto the lead body 510 or can be used as a part of the lead body 510 to separate the electrodes. The lead 500 may also include an end spacer (not shown). The end spacer is disposed at the distal end of the lead 500. The end spacer may have any shape, but is preferably rounded at the distal end. The spacers 520 and the end spacer can be made of any non-conductive biocompatible material including, for example, silicone, polyurethane, and polyetheretherketone (PEEK). The spacers 520 help electrically isolate the pre-electrodes 600. Additionally or alternatively, the pre-electrodes can be disposed over portions of a contiguous, non-conducting lead body 510 with an opening through the lead body 510 to allow the conductors 540 to be coupled to the pre-electrodes 600.

In some embodiments, the outer diameter of the pre-electrodes 600 may be the same as the outer diameter of the spacers. In some other embodiments, the outer diameter of the pre-electrodes 600 may alternatively be greater than the outer diameter of the spacers 520 such that the pre-electrodes 600 are raised above the spacers 520. Alternatively, the outer diameter of the spacers 520 may be greater than the outer diameter of the pre-electrodes 600 such that the pre-electrodes are recessed.

An assembly may be subject to a reflow operation after all the spacers 520 and pre-electrodes 600 have been loaded onto the lead body 510 and attached to conductors 540 as necessary. The reflow operation is useful in attaching the spacers 500 and pre-electrodes 600 to the lead body 510 and improves structural integrity of the assembly and leads to improved reliability.

Figure 7:
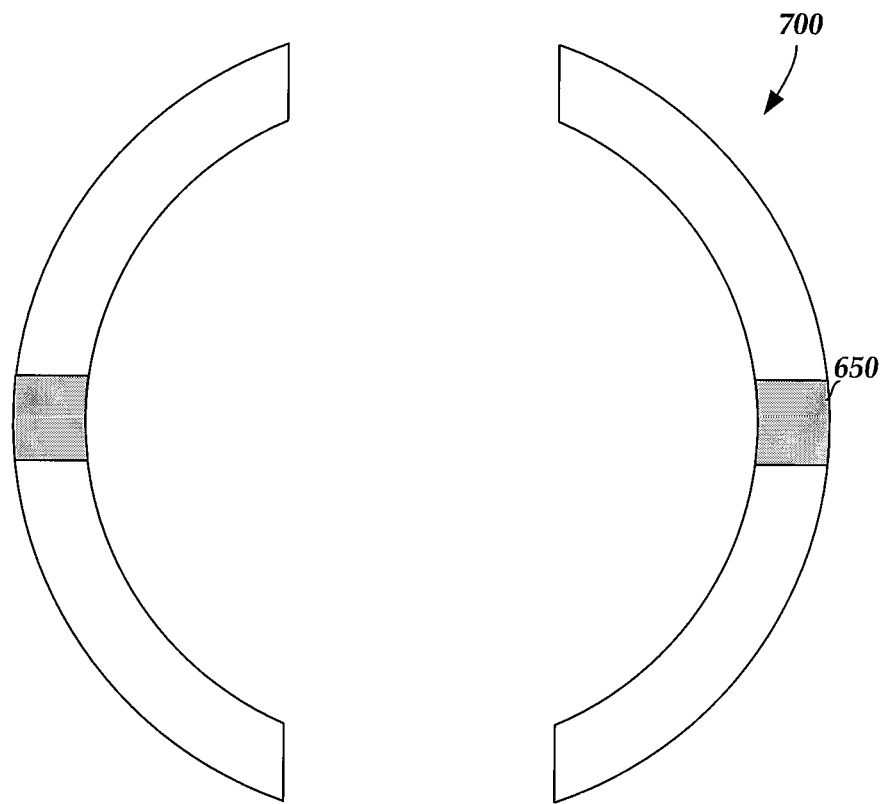
FIG. 7 is a schematic cross-sectional view of the pre-electrode of FIG. 6 after the thin-walled portions have been removed to create two segmented electrodes, according to the invention.

The lead 500 may then be further processed to remove portions of the pre-electrodes 600. In some embodiments, the lead 500 is centerless ground to remove portions of the outer diameter 640 (e.g. to remove the thin-walled portions 610), although it will be understood that any suitable method can be used to remove these portions including cutting, skiving or laser ablation. FIG. 7 is a schematic cross-sectional view of the pre-electrode 600 of FIG. 6 after the thin-walled portions 610 have been removed. As seen in FIG. 7, the result of removing the thin-walled portions is that two segmented electrodes 700 are formed. Thus, the thin-walled portions 610 and thick-walled portions 620 may be arranged so that any configuration of segmented electrodes 700 is formed after grinding. It will be appreciated that the slotted positions 650 can also be arranged so that each segmented electrode 700 is connected to a conductor after the grinding process.

Figure 8:
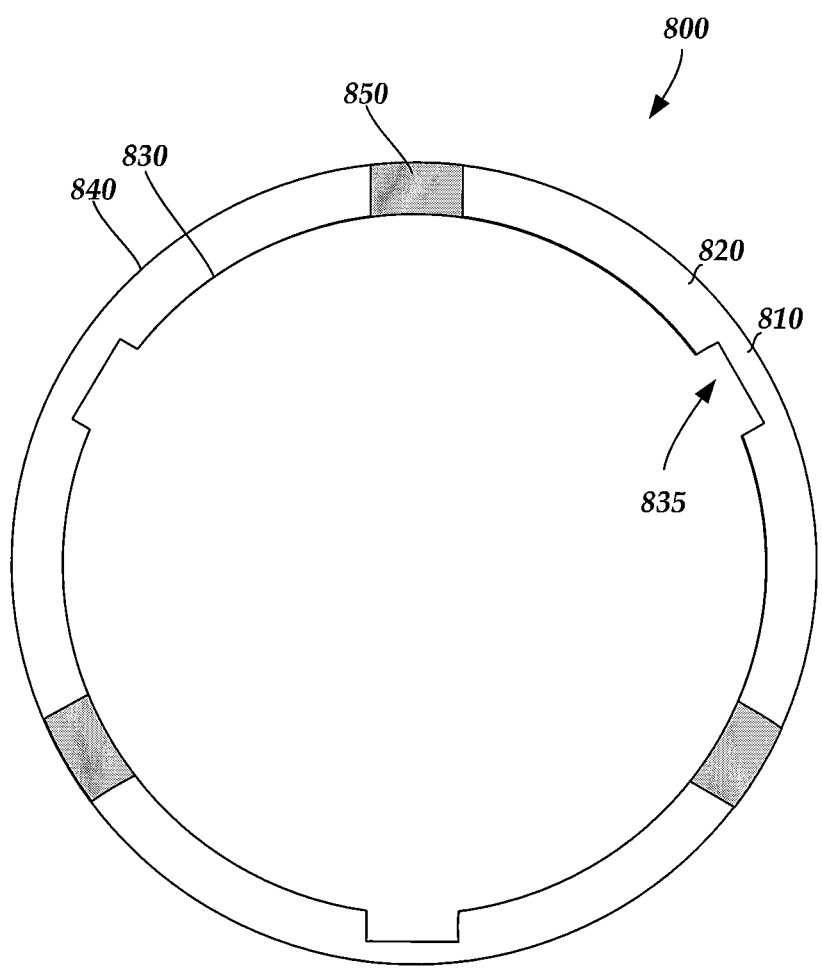
FIG. 8 is a schematic cross-sectional view of a pre-electrode having three thin-walled portions separated by three thick-walled portions, according to the invention.
Figure 9:
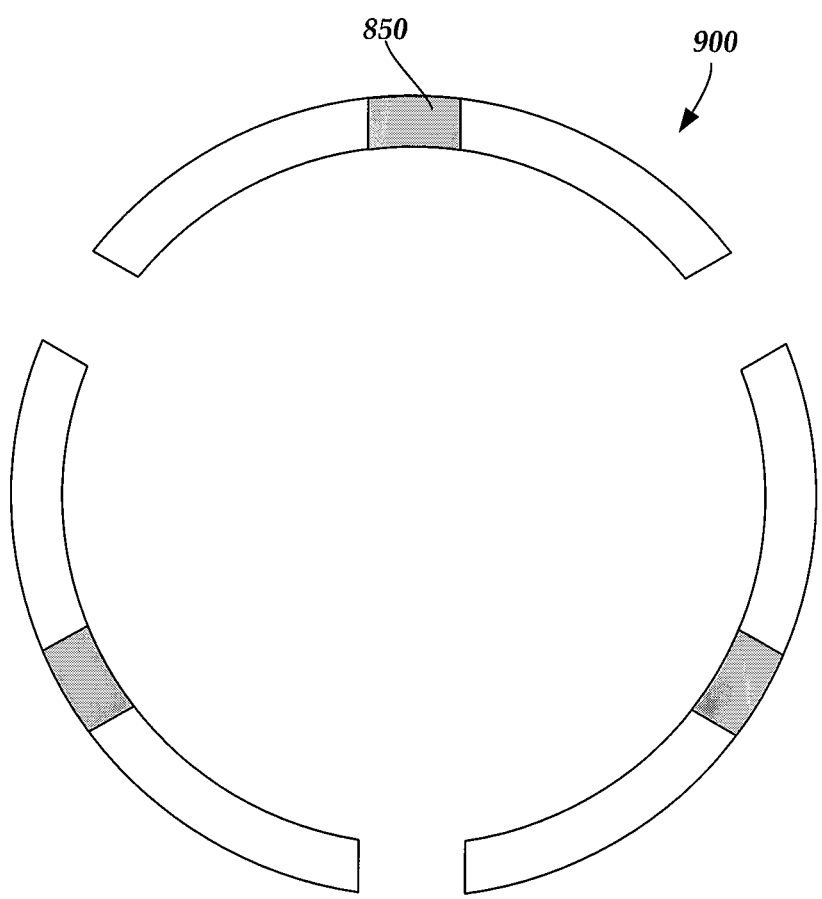
FIG. 9 is a schematic cross-sectional view of the pre-electrode of FIG. 8 after the thin-walled portions have been removed to create three segmented electrodes, according to the invention.

FIG. 8 is a schematic cross-sectional view of a pre-electrode 800 having three thin-walled portions 810 separated by three thick-walled portions 820. The pre-electrode 800 has an inner diameter 830 and an outer diameter 840. As seen in FIG. 8, the inner diameter has three keyed portions 835. As seen in FIG. 9, the pre-electrode 800 of FIG. 8 is able to form three segmented electrodes 900 when the thin-walled portions have been removed using the methods described above. In some embodiments, the three segmented electrodes 900 are of the same size. In at least some other embodiments, the keyed portions 835 will be arranged so that segmented electrodes 900 of different sizes are produced after the grinding process. Furthermore, the keyed portions may be arranged so that each segmented electrode includes a slotted position 850 for connected to a conductor. It will be understood that any number of segmented electrodes may be formed in this manner. For example, leads having four, five, six, seven, eight, ten, twelve or sixteen radially arranged segmented electrodes may be produced using these methods.

Figure 10A:
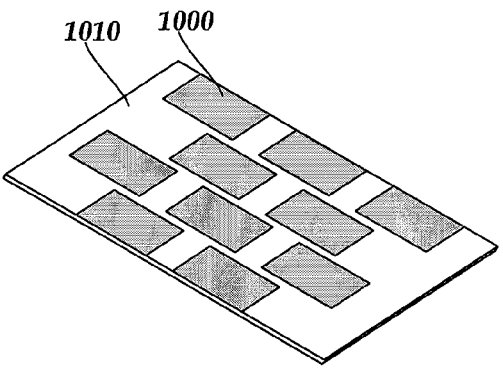
FIG. 10A is a schematic perspective view of a plurality of electrodes coupled to a plate, according to the invention.

In at least some other embodiments, radially segmented electrode arrays are formed starting with a plate. FIG. 10A is a schematic perspective view of a plurality of electrodes 1000 coupled to a plate 1010. The plurality of electrodes 1000 may be coupled to the plate 1010 using any suitable method, such as resistance welding, laser welding, adhesive or the like. In some embodiments, the plate 1010 is an iron plate, although any suitable metal may be used that is capable of acting as a support structure and being removed by any of the processes described above (e.g., by a selective etching process.)

The plurality of electrodes 1000 may be disposed on the plate 1010 in any desired arrangement. For example, in some embodiments, the plurality of electrodes 1000 are divided into equally spaced rows on the plate 1010. Each row may include the same number or a different number of electrodes. In some embodiments, the rows include a different number of electrodes. The rows may also be offset from one another, such that electrodes are not longitudinally aligned. The spacing between electrodes may also vary within rows or between rows. In at least some other embodiments, the plurality of electrodes 1000 are disposed on the plate 1010 in a circular arrangement, a diagonal arrangement, or in any other desired pattern.

Conductors (not shown) are then joined to the plurality of electrodes 1000 by welding or other techniques. In some embodiments, each individual electrode is connected to a separate and distinct conductor. In at least some other embodiments, multiple electrodes are connected to the same conductor.

Figure 10B:
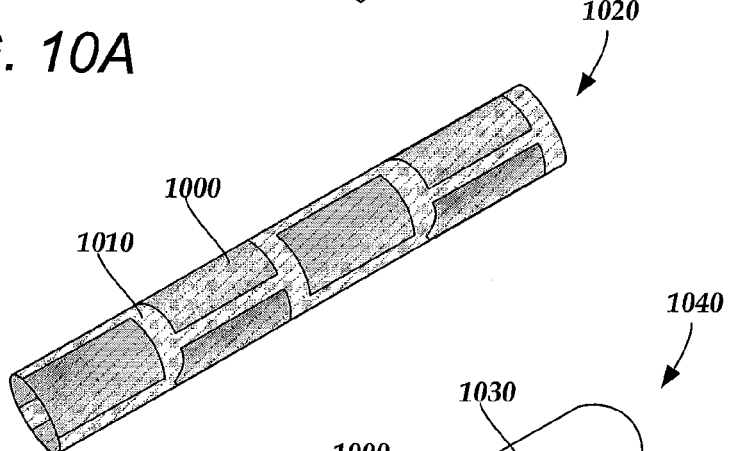
FIG. 10B is a schematic perspective view of the plurality of electrodes coupled a plate after the plate has been formed into a cylinder, according to the invention.

In some embodiments, the plate 1010 is then formed into a cylinder. In some embodiments, in order to create a cylinder, a mandrel is placed along the midline of the plate 1010 and inserted into the central lumen of a lead body of the proximal end sub-assembly. The plate 1010 may then be drawn through a die, or a series of dies to form the desired cylindrical shape. The cylinder may be formed so that conductors, still attached to the plurality of electrodes 1000, extend through the central lumen of the cylinder. FIG. 10B is a schematic perspective view of the plurality of electrodes 1000 coupled a plate 1010 after the plate 1010 has been formed into a cylinder 1020.

Figure 10C:
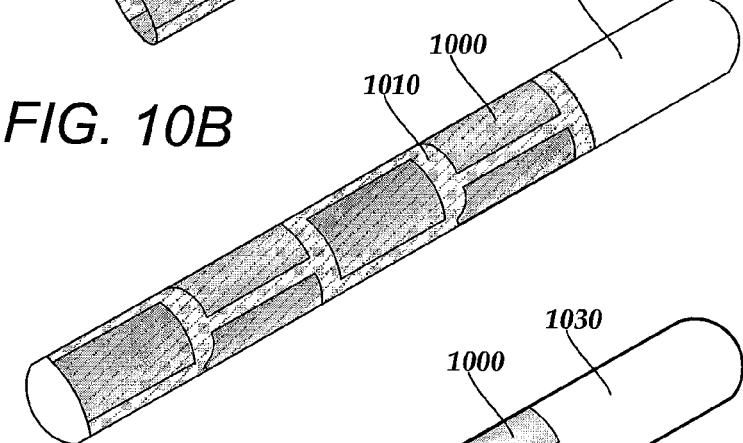
FIG. 10C is a schematic perspective view of the cylinder of FIG. 10B after its lumen has been filled with an insulative material to create a lead assembly, according to the invention.

The newly-formed cylinder 1020 includes a hollow central lumen with the conductors extending through the lumen. The central lumen of the cylinder 1020 may be filled with an insulative or polymeric material to create a lead body 1030. As previously indicated, suitable polymeric materials include, but are not limited to, silicone, polyurethane, and polyethylene. FIG. 10C is a schematic perspective view of the cylinder of FIG. 10B after its lumen has been filled with an insulative material to create a lead assembly 1040. In some embodiments, a liquid silicone rubber is injected into the cylinder 1020 to form a lead body 1030.

Figure 10D:
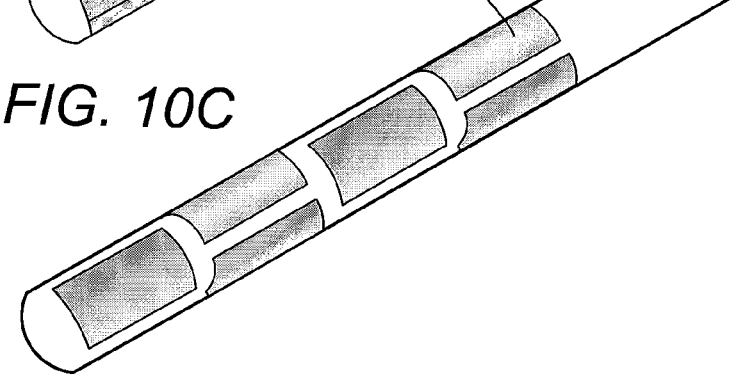
FIG. 10D is a schematic perspective view of the cylinder of FIG. 10C after the plate has been removed, according to the invention.

After the cylinder 1020 has been injected with an insulative material to form a lead assembly 1040, the lead assembly 1040 may then be subjected to a series of steps to cure it. The plate 1010 is then removed from the lead assembly 1040 to expose the plurality of electrodes 1000. In some embodiments, the lead assembly 1040 is placed in an acid bath to dissolve the plate 1010. Alternatively, any suitable technique may be used to remove the plate 1010 from the lead assembly 1040. FIG. 10D is a schematic perspective view of the cylinder of FIG. 10C after the plate 1010 has been removed. The lead assembly 1040 includes a plurality of electrodes 1000 in a radial arrangement corresponding to the arrangement chosen for welding the plurality of electrodes 1000 to the plate 1010.

It will be understood that in some embodiments, a lead is formed using a variety of materials. For example, the material injected into the cylinder 1020 need not be the same material used throughout the rest of the lead. The choice of materials for lead construction can depend on a variety of factors including, for example, biocompatibility, mechanical properties (e.g., flexibility, tensile strength, tear strength, and elongation), biostability, handling properties, ease of manufacture, cost, production time, and the like. Thus, leads can be produced using different materials along different parts of the lead. For example, a distal end can be made of one material, for example, silicone or polyurethane, and the proximal end of the lead can be made using another material, for example, polyurethane or PEEK. As one example, silicone may be selected for the distal end of the lead because it is a more flexible material. Polyurethane may be selected for the proximal end because it is stiffer and provides better stiffness that improves insertion into a control module (e.g., an implantable pulse generator) or a lead connector. In these leads, the two portions of the lead made of different materials couple together at a transition site. The transition site can generally be any suitable site along the length of the lead between the proximal and distal ends. Transition sites can also occur even when the two portions of the lead are made of the same material and later joined together. It will be recognized that the transition site can be positioned at any point along the lead and that a lead may contain more than one transition site.

In some embodiments, a sleeve over the transition site is used to couple the two portions of the lead together. A sleeve, however, may increase the diameter of the lead at the transition site which may be undesirable, particularly because a larger diameter introducer may be needed to accommodate the larger diameter of the lead at the transition site.

In at least some other embodiments, instead of a sleeve, the two portions of the lead at the transition site can be coupled by modifying the ends of the portions to form a connecting arrangement. The lead includes a first lead portion, for example, the portion injected into the cylinder 1020, made of a first material and a second lead portion made of second material. For example, the first material can be silicone and the second material can be a polyurethane, or vice versa. It will be recognized that the first lead portion can be either the distal or proximal portion of the lead and that the second lead portion is then the proximal or distal portion of the lead, respectively.

Figure 11A:
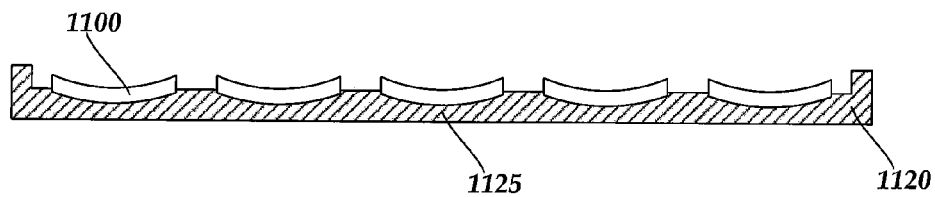
FIG. 11A is a schematic cross-sectional view of one embodiment of an array of electrodes positioned within a carrier mold, according to the invention.
Figure 11B:
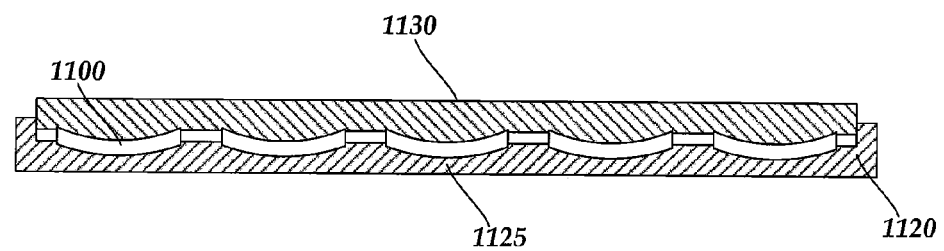
FIG. 11B is a schematic cross-sectional view of the carrier mold and the array of electrodes of FIG. 11A after a carrier mold cover has been placed over the carrier mold, according to the invention.
Figure 11C:
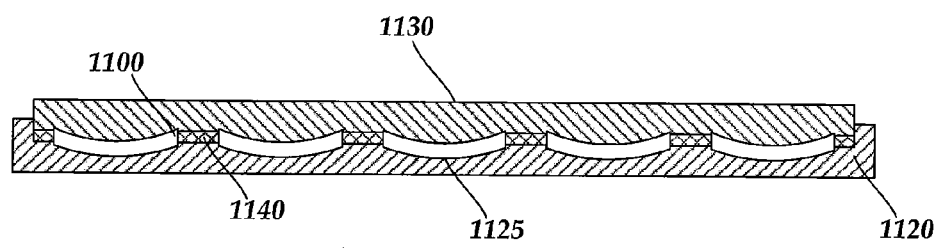
FIG. 11C is a schematic cross-sectional view of the assembly of FIG. 11B after a carrier has been molded around the array of electrodes, according to the invention.
Figure 11D:
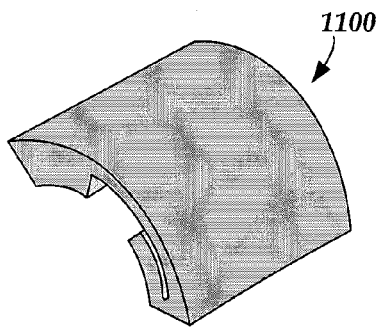
FIG. 11D is a schematic perspective view of an electrode overmolded in a liquid injection molding carrier, according to the invention.

FIG. 11D is a schematic perspective view of one embodiment of an electrode 1100 that can be molded into a carrier using liquid injection molding. This process will be described in greater detail with reference to FIGS. 11A-11C. As seen in FIG. 11A, the electrodes 1100 may be placed in the desired array arrangement by positioning the electrodes 1100 in a carrier mold 1120. In some embodiments, the electrodes 1100 are curved as seen in FIGS. 11A-D. In at least some other embodiments, the electrodes 1100 are flat when placed in the carrier mold, and later formed into the desired shape. Suitable materials for the carrier mold 1120 include, but are not limited to, metal, polymers (including plastics), composite materials, and the like. Preferably, the carrier mold 1120 is made of a durable material that allows the carrier mold 1120 to be reused. In some embodiments, the carrier mold 1120 is curved or cylindrical. The electrodes 1100 may be disposed in the carrier mold in any suitable arrangement. The electrodes 1100 may, for example, be placed in two, three, or four columns within the carrier mold 1120 and each column may contain any number of electrodes. Because a carrier may be wrapped around a mandrel, columns of electrodes 1100 disposed within a carrier mold 1120 may coincide with a circumferential electrode arrangement as seen in FIG. 1.

The carrier mold 1120 may include electrode positioning features 1125, e.g., indentations or depressions in the carrier mold 1120, that are disposed in the desired array arrangement. The electrode positioning features 1125 aid positioning of the electrodes 1100 in the pre-determined arrangement. For example, the electrodes 1100 may be placed in a carrier mold 1120 that has indentations in the bottom of the mold that accommodate the shape of the electrodes 1100 and keep the electrodes 1100 in position during the process of manufacturing the carrier. The electrodes 1100 may be concave and the carrier mold 1120 may have indentations that accommodate the concave shape of the electrodes 1100. Preferably, at least a portion of the side surface of the electrodes 1100 remains exposed within the carrier mold 1120.

As can be appreciated from FIG. 11B, after the electrodes 1100 are positioned in the carrier mold 1120, a carrier mold cover 1130 may be placed over the electrodes 1100 and the carrier mold 1120. Suitable materials for the carrier mold cover 1130 include, but are not limited to, metal, polymers (including plastics), composite materials, and the like. Preferably, the carrier mold cover 1130 is made of a durable material, such as metal, that allows the carrier mold cover 1130 to be reused.

FIG. 11C is a schematic cross-sectional view of the assembly of FIG. 11B after a carrier 1140 has been molded around the array of electrodes 1110. The carrier 1140 can be made of any biocompatible material including, for example, silicone, polyurethane, polyetheretherketone (PEEK), epoxy, and the like.

The carrier 1140 may be formed by any process including, for example, molding (including injection molding), casting, and the like. In some embodiments, the carrier 1140 is formed by injection molding. After the carrier 1140 is molded around the electrodes 1100, conductors (not shown) are joined to the electrodes 1100 positioned in the carrier 1140. Optionally, the intermediate assembly, which includes the completed carrier and the array of electrodes 1100, can be removed from the carrier mold 1120 before the conductors are coupled to the electrodes 1100. The carrier 1140 with welded cables is then wrapped around a mandrel to create a substantially cylindrical shape and placed into an overmold. The assembly is then overmolded forming a radially segmented electrode array.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of making a lead for a stimulation device comprising:
    coupling a plurality of electrodes to a plate;
    joining individual conductors to each of the plurality of electrodes;
    after joining the conductors to the electrodes, placing a mandrel along the midline of the plate;
    forming the plate around the mandrel and into a cylinder with the conductors extending through a hollow central lumen of the cylinder;
    filling the hollow central lumen of the cylinder with an insulative material to create a lead assembly; and
    removing the plate to expose the plurality of electrodes.

2. The method of claim 1, wherein forming the plate into a cylinder comprises
    drawing the plate through at least one die to form a substantially cylindrical shape.

3. The method of claim 1, wherein coupling a plurality of electrodes to a plate comprises coupling a plurality of the electrodes to an iron plate.

4. The method of claim 1, wherein coupling a plurality of electrodes to a plate comprises resistance welding sets of the electrodes at multiple levels on the plate, wherein each set of the electrodes is aligned with an adjacent set of the electrodes.

5. The method of claim 1, wherein coupling a plurality of electrodes to a plate comprises resistance welding sets of the electrodes at multiple levels on the plate, wherein adjacent sets of the electrodes are staggered.

6. The method of claim 1, wherein removing the plate comprises placing the lead assembly in an acid bath to dissolve the plate.

7. The method of claim 1, wherein coupling a plurality of electrodes to a plate comprises coupling the plurality of electrodes in an arrangement with a plurality of rows, wherein each row has a plurality of the electrodes.

8. The method of claim 7, wherein the plurality of rows are arranged so that adjacent rows are offset from one another.

9. The method of claim 1, wherein coupling the plurality of electrodes to the plate comprises coupling the plurality of the electrodes to the plate using an adhesive.

10. A method of making a lead for a stimulation device comprising:
    coupling a plurality of electrodes to a plate using an adhesive;
    joining individual conductors to each of the plurality of electrodes;
    forming the plate into a hollow cylinder with the conductors extending through a hollow central lumen of the cylinder;
    filling the hollow central lumen of the hollow cylinder with an insulative material to create a lead assembly; and
    removing the plate to expose the plurality of electrodes.

11. The method of claim 10, wherein forming the plate into a hollow cylinder comprises:
    placing a mandrel along the midline of the plate; and
    drawing the plate through at least one die to form a substantially cylindrical shape.

12. The method of claim 10, wherein coupling a plurality of electrodes to a plate comprises coupling a plurality of the electrodes to an iron plate.

13. The method of claim 10, wherein coupling a plurality of electrodes to a plate comprises coupling sets of the electrodes at multiple levels on the plate, wherein each set of the electrodes is aligned with an adjacent set of the electrodes.

14. The method of claim 10, wherein coupling a plurality of electrodes to a plate comprises coupling sets of the electrodes at multiple levels on the plate, wherein adjacent sets of the electrodes are staggered.

15. A method of making a lead for a stimulation device comprising:
    coupling a plurality of electrodes to a plate;
    joining individual conductors to each of the plurality of electrodes;
    forming the plate into a hollow cylinder with the conductors extending through a hollow central lumen of the cylinder;
    filling the hollow central lumen of the hollow cylinder with an insulative material to create a lead assembly; and
    removing the plate to expose the plurality of electrodes.

16. The method of claim 15, wherein forming the plate into a hollow cylinder comprises:
    placing a mandrel along the midline of the plate; and
    drawing the plate through at least one die to form a substantially cylindrical shape.

17. The method of claim 15, wherein coupling a plurality of electrodes to a plate comprises coupling a plurality of the electrodes to an iron plate.

18. The method of claim 15, wherein coupling a plurality of electrodes to a plate comprises coupling sets of the electrodes at multiple levels on the plate, wherein each set of the electrodes is aligned with an adjacent set of the electrodes.

19. The method of claim 15, wherein coupling a plurality of electrodes to a plate comprises coupling sets of the electrodes at multiple levels on the plate, wherein adjacent sets of the electrodes are staggered.

* * * * *